United States Patent
Askill

(10) Patent No.: US 6,974,585 B2
(45) Date of Patent: Dec. 13, 2005

(54) DURABLE MULTI-COMPONENT ANTIBIOTIC FORMULATION FOR TOPICAL USE

(75) Inventor: Ian N. Askill, Colorado Springs, CO (US)

(73) Assignee: MedLogic Global Limited, Cheshire (GB)

( * ) Notice: Subject to any disclaimer, the term of this patent is extended or adjusted under 35 U.S.C. 154(b) by 86 days.

(21) Appl. No.: 10/208,199

(22) Filed: Jul. 31, 2002

(65) Prior Publication Data

US 2003/0031717 A1 Feb. 13, 2003

Related U.S. Application Data

(60) Provisional application No. 60/308,863, filed on Aug. 1, 2001.

(51) Int. Cl.$^7$ ............................................... A01N 25/24
(52) U.S. Cl. ........................ 424/407; 424/405; 424/422; 424/423; 424/484; 424/487; 424/78.06; 424/78.07; 424/78.08; 424/78.35; 424/78.37; 523/122; 514/9
(58) Field of Search ................................ 424/405, 407, 424/411, 422, 423, 484, 487, 78.06–78.08, 78.35, 78.37; 523/122; 526/89, 310; 514/9

(56) References Cited

U.S. PATENT DOCUMENTS

| | | | |
|---|---|---|---|
| 3,654,239 A | 4/1972 | McIntire et al. |
| 5,254,132 A | 10/1993 | Barley et al. |
| 5,306,490 A | 4/1994 | Barley |
| 5,403,591 A | 4/1995 | Tighe et al. |
| 5,580,565 A | 12/1996 | Tighe et al. |
| 5,653,769 A | 8/1997 | Barley, Jr. et al. |
| 5,684,042 A | 11/1997 | Greff et al. |
| 5,807,563 A | 9/1998 | Askill et al. |
| 5,962,010 A | 10/1999 | Greff et al. |
| 6,238,692 B1 | 5/2001 | Smith |
| 6,342,213 B1 | 1/2002 | Barley et al. |

FOREIGN PATENT DOCUMENTS

| | | | |
|---|---|---|---|
| EP | 0 856 318 A1 | | 8/1998 |
| EP | 0 858 810 A2 | | 8/1998 |
| EP | 0858810 | * | 8/1998 |
| WO | 99/23150 | * | 5/1999 |

* cited by examiner

*Primary Examiner*—Neil S. Levy
(74) *Attorney, Agent, or Firm*—Foley & Lardner LLP

(57) ABSTRACT

Disclosed are methods and formulations for the treatment or prevention of infections on mammalian tissues such as skin. Specifically, the methods of this invention involve the in situ formation of a polymeric cyanoacrylate film containing mixed antibiotics over mammalian tissue.

15 Claims, No Drawings

DURABLE MULTI-COMPONENT ANTIBIOTIC FORMULATION FOR TOPICAL USE

CROSS-REFERENCE TO RELATED APPLICATIONS

This application claims the benefit of U.S. Provisional Patent Application Ser. No. 60/308,863 filed Aug. 1, 2001 which application is incorporated herein by reference in its entirety.

BACKGROUND OF THE INVENTION

1. Field of the Invention

This invention is directed to methods and formulations for the treatment or prevention of infections on mammalian tissues such as skin. Specifically, the methods of this invention involve the in situ formation of a polymeric cyanoacrylate film containing mixed antibiotics over mammalian tissue.

2. References

The following patents are cited in this application as superscript numbers:

[1] Barley, "*Methods for Retarding Blister Formation by Use of Cyanoacrylate Adhesives*", U.S. Pat. No. 5,306, 490, issued Apr. 26, 1994.

[2] Barley, et al., *Methods for Treating Suturable Wounds by Use of Sutures and Cyanoacrylate Adhesives*, U.S. Pat. No. 5,254,132, issued Oct. 19, 1993

[3] McIntire, et al., *Process for the Preparation of Poly (α-Cyanoacrylates)*, U.S. Pat. No. 3,654,239, issued Apr. 4, 1972

[4] Barley, et al., *Methods for Treating Non-Suturable Wounds by Use of Cyanoacrylate Adhesives*, U.S. Pat. No. 6,342,213, issued Jan. 29, 2002.

[5] Barley, et al., *Methods for Reducing Skin Irritation From Artificial Devices by Use of Cyanoacrylate Adhesives*, U.S. Pat. No. 5,653,789, issued Aug. 5, 1997

[6] Tighe, et al., *Methods for Inhibiting Skin Ulceration by Use of Cyanoacrylate Adhesives*, U.S. Pat. No. 5,403, 591, issued Apr. 4, 1995

[7] Tighe, et al., for *Use of Cyanoacrylates for Providing a Protective Barrier*, U.S. Pat. No. 5,580,565, issued Dec. 6, 1996

[8] Askill, et al., for *Methods for Draping Surgical Incision Sites*, U.S. Pat. No. 5,807,563 issued Sep. 15, 1998

[9] Greff, et al., for *Cyanoacrylate Compositions Comprising an Antimicrobial Agent*, U.S. Pat. No. 5,684,042, issued Nov. 3, 1997

All of the above patents are herein incorporated by reference in their entirety to the same extent as if each individual patent was specifically and individually indicated to be incorporated by reference in its entirety.

3. State of the Art

Many commercial topical antibiotic preparations exist in creams, lotions, petroleum bases, etc. While they are easily applied, they are also easily rubbed off (e.g., ointments applied to the skin frequently rub off onto the patient's clothing within minutes or hours thereby losing their effectiveness). This problem is most commonly addressed by applying protective layers or covers such as dressings over the ointments.

The covers, while simple to use, can absorb the ointment or cause it to displace to another area. The ointment can also prevent the adhesive on the dressing from effectively adhering. In some cases, attempts have been made to incorporate the active ingredients in pre-formed films or in film-forming solutions. Unfortunately, most preformed films have limited diffusion of the active ingredients and show little or no clinical activity.

Greff, et al.[9] have demonstrated that certain iodophors can be incorporated into prepolymeric cyanoacrylate compositions to create stable film forming liquids wherein the iodophor effectively provides for antimicrobial activity to the polymer film formed therefrom. However, many antimicrobial agents are incompatible with prepolymeric cyanoacrylate compositions causing either immediate polymerization or preventing polymerization from occurring at all or within a reasonable period of time after application to mammalian tissue. In addition, while insoluble antibiotics appear to cause less rapid effects on the performance of the prepolymeric cyanoacrylate compositions, these materials will most frequently fall out of suspension and resist re-suspension. This is particularly disadvantageous where the mixing potential is restricted by the size of the container, e.g., a single use package.

Heretofore, prepolymeric cyanoacrylate compositions have been disclosed for use in a variety of medical environments such as an alternative or adjunct to sutures[2] or as a hemostat[3]. Other described uses of cyanoacrylate prepolymers include their use on mammalian tissue to form polymeric films which are utilized:

to prevent friction blister formation[1], in treating small non-suturable wounds[4], in inhibiting surface skin irritation arising from friction between the skin surface and artificial devices such as tapes, prosthetic devices, casts, etc.[5], as surgical incise drapes[8], in inhibiting skin ulceration[6], and forming a protective film to inhibit skin degradation due to incontinence.[7]

In each case, the combination of conventional antibiotics with these compositions would be useful particularly as a replacement for conventional bandages.

SUMMARY OF THE INVENTION

This invention is directed, in part, to polymerizable cyanoacrylate compositions comprising one or more insoluble antibiotics. In particular, these compositions comprise a sufficient amount of a thickening agent to form a stable suspension or gel. These compositions are useful in methods for covering mammalian tissue with a polymeric antibacterial film which reduces the risk of infection to the underlying and/or adjacent tissue and, in the case of mammalian skin, forms a waterproof film over the skin.

This invention is also directed, in part, to methods for the treatment or prevention of infections in mammalian tissue which methods involve formation of an antibacterial cyanoacrylate polymeric film over mammalian tissue by the in situ polymerization of the polymerizable cyanoacrylate composition. This composition can be applied as a liquid/gel to the skin surface and can include additional therapeutic agents such as analgesics, anti-inflammatory agents, and the like.

Accordingly, in one of its composition aspects, this invention is directed to a polymerizable film-forming cyanoacrylate composition comprising:

from about 50 to 99 weight percent of a polymerizable cyanoacrylate ester based on the total weight of the composition;

an antibacterially effective amount of an antibiotic or mixture of antibiotics which are insoluble in the polymerizable cyanoacrylate ester; and a sufficient amount of a thickening agent which forms a stable suspension or gel in combination with the cyanoacrylate ester and the antibiotic or the mixture of antibiotics.

Preferably, the antibiotic employs a mixture of antibiotics in order to provide a full spectrum of activity and, more preferably, this mixture is employed at from about 0.01 to about 2 weight percent based on the total weight of the composition.

Preferably, the thickening agent is employed in an amount ranging from about 0.5 to about 10 weight percent based on the total weight of the composition.

Accordingly, in another of its composition aspects, this invention is directed to a film-forming cyanoacrylate composition comprising:

from about 50 to 99 weight percent of a polymerizable cyanoacrylate ester based on the total weight of the composition;

from about 0.01 to about 2 weight percent of a mixture of antibiotics which are insoluble in the polymerizable cyanoacrylate ester; and from about 0.5 to about 10 weight percent of a thickening agent which forms a stable suspension or gel in combination with the cyanoacrylate ester and the mixture of antibiotics.

In one of its method aspects, this invention is directed to a method for the treatment or prevention of infections on mammalian tissues which method comprises:

(a) identifying bacterially infected mammalian tissue or tissue at risk of such infection;

(b) applying to the mammalian tissue identified in (a) above a sufficient amount of a composition comprising:

from about 50 to 99 weight percent of a polymerizable cyanoacrylate ester based on the total weight of the composition;

an antibacterially effective amount of an antibiotic or mixture of antibiotics which are insoluble in the polymerizable cyanoacrylate ester; and a sufficient amount of a thickening agent which forms a stable suspension or gel in combination with the cyanoacrylate ester and the antibiotic or the mixture of antibiotics; and (c) polymerizing the cyanoacrylate ester so as to form an adherent polymeric film on the tissue where the composition was applied.

Preferably, the polymerizable cyanoacrylate ester comprises an ester which, in monomeric form, is represented by formula I:

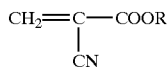

where R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

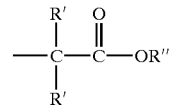

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula I, R is alkyl of from 2 to 10 carbon atoms and more preferably alkyl of from 2 to 8 carbon atoms. Even more preferably, R is butyl, pentyl or octyl and most preferably, R is n-butyl.

In another preferred embodiment, the polymerized cyanoacrylate composition has a thickness of no more than about 1 millimeter and, more preferably, the polymer layer has a thickness of from about 2 to about 500 microns and still more preferably from about 20 to about 100 microns.

DETAILED DESCRIPTION OF THE PREFERRED EMBODIMENTS

This invention is directed to methods and formulations for the treatment or prevention of infections on mammalian tissues such as skin. However, prior to discussing this invention in further detail, the following terms will first be defined.

Definitions

As used herein, the following terms have the following meanings:

The term "polymerizable cyanoacrylate esters" refers to polymerizable formulations comprising cyanoacrylate monomers or polymerizable oligomers which, in their monomeric form, are preferably compounds represented by formula I as described above.

More preferably, in formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, pentyl or octyl and most preferably, R is n-butyl. Mixtures of such compounds can also be employed as disclosed by Berger, et al., U.S. Pat. No. 5,998,472 which is incorporated herein by reference in its entirety.

A preferred cyanoacrylate ester for use in the invention is n-butyl-2-cyanoacrylate.

The polymerizable cyanoacrylate esters described herein rapidly polymerize in the presence of water vapor or tissue protein, and the n-butyl-cyanoacrylate bonds to mammalian skin tissue without causing histotoxicity or cytotoxicity.

Such polymerizable cyanoacrylate esters are sometimes referred to herein as prepolymers and compositions comprising such esters are sometimes referred to herein as prepolymer compositions.

Polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

The term "biocompatible plasticizer" refers to any material which is soluble or dispersible in the cyanoacrylate composition, which increases the flexibility of the resulting polymeric film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate, acetyl tri-hexyl citrate, butyl benzyl phthalate, dibutyl phthalate, dioctylphthalate, n-butyryl tri-n-hexyl citrate, diethylene glycol dibenzoate, and the like. The particular biocompatible plasticizer employed is not critical and preferred plasticizers include dioctylphthalate and $C_2$–$C_4$-acyl tri-n-hexyl citrates.

The term "thickening agent" refers to any biocompatible material which increases the viscosity of the composition. Suitable thickening agents include, by way of example, polymethyl methacrylate (PMMA) or other preformed polymers soluble or dispersible in the composition, a suspending agent such as fumed silica and the like with PMMA being preferred. Fumed and modified fumed silica are particularly useful in producing a gel for topical application having a viscosity of from about 1,500 to about 1,000,000 centipoise at 20° C. Suitable thickening agents for the compositions described herein also include a partial polymer of the alkyl cyanoacrylate as disclosed in U.S. Pat. Nos. 3,654,239 and 4,038,345 both of which are incorporated herein by reference in their entirety.

Thickening agents are deemed to be biocompatible if they are soluble or dispersible in the composition and are compatible with the skin as measured by the lack of moderate to severe skin irritation.

The phrase "antibiotic or mixture of antibiotics which are insoluble in the polymerizable cyanoacrylate ester" refers to those antibiotics which individually or in admixture have a solubility of less than 0.01 mg/mL of cyanoacrylate ester at 20° C. Suitable antibiotics include bacitracin zinc, polymyxin B sulfate, neomycin sulfate, and the like.

The term "stable suspension" refers to suspensions wherein at least 50 percent, and preferably at least 90%, of the suspended material remains in suspension for a period of at least 3 months and, preferably at least 6 months, at 20° C.

Methods

The methods of this invention comprise the in situ formation of an antibacterial, cyanoacrylate polymer film on mammalian tissue such as mammalian skin.

The treatment protocol preferably involves tissue preparation prior to in situ formation of the cyanoacrylate polymer. For example, mammalian skin is first conventionally treated by the attending health care professional by cleaning with an appropriate antimicrobial composition. The skin is preferably dried, e.g., blotted dry, and then an adherent antibacterial polymeric film is formed over this site by applying a cyanoacrylate composition of this invention. As noted above, this composition comprises polymerizable cyanoacrylate monomers and/or reactive oligomers which, upon contact with the skin, polymerizes in situ to form a polymeric film. Pretreatment of other mammalian tissue will also follow conventional procedures.

Polymerization occurs at ambient conditions for a sufficient period of time to allow robust films to form. In general, the particular length of time required for polymerization will vary depending on factors such as the amount of adhesive composition applied, the temperature of the tissue, the moisture content of the tissue, the surface area of tissue, and the like. However, in a preferred embodiment, polymerization is generally complete within about 10 to about 60 seconds while the tissue is maintained at ambient conditions; however, in some cases, polymerization can occur up to about 5 minutes. During this period, the tissue is maintained in a position which permits the cyanoacrylate to polymerize and form a polymeric film while minimizing any movement which might dislodge the cyanoacrylate from the tissue or create undesirable bonding.

Sufficient amounts of the composition are employed to cover (i.e., coat) the entire tissue site with a layer of the cyanoacrylate polymer. If necessary, excess cyanoacrylate monomer and/or oligomer can be removed with a wipe or tissue paper before polymerization or, after polymerization, any polymer formed at unintended sites can be removed with materials such as acetone.

After polymerization, the resulting polymeric film forms an antibacterial, barrier film which strongly adheres to the skin, is flexible and waterproof. Such strong adherence effectively eliminates the possibility that the film will separate from the tissue. In the case of application to mammalian skin, the polymeric film will only adhere to the skin for a period of about 1–4 days after which time it sloughs off. This occurs because the cyanoacrylate polymer is adhering only to the epidermal layer which is continuously in the process of being sloughed off and replaced by the underlying cells. Accordingly, the cyanoacrylate film need not be removed from such skin.

The polymeric film should be maintained in an unbroken manner over the entire tissue. This can be assured by careful application of the cyanoacrylate adhesive onto the tissue. Additionally, the use of a plasticizer will facilitate the maintenance of the polymeric film in an unbroken manner and will inhibit cracking of the film.

In one embodiment, after application of the initial polymeric layer, a second, preferably thinner, layer is applied thereto. Additional amounts of cyanoacrylate composition can be applied as needed to maintain an unbroken coating covering over the tissue.

Application is conducted under conditions wherein the polymeric film preferably has a thickness of no more than about 1 millimeter and, more preferably, the polymer layer has a thickness of from about 2 to about 500 microns and still more preferably from about 20 to about 100 microns. If thinner polymeric films are desired, then the polymeric film should have a thickness of from about 2 to about 50 microns and preferably from 10 to 40 microns. The amount of cyanoacrylate composition applied to a unit area to obtain such thicknesses is well within the skill of the art.

The size and thickness of the polymeric film formed onto the tissue area can be readily controlled by the amount and viscosity of cyanoacrylate adhesive composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is one example of a dispenser which dispenses the cyanoacrylate adhesive composition in a controlled dropwise manner. Other methods for the controlled dispersement of the cyanoacrylate adhesive include, by way of example, a spray applicator, brush, wipe, swab or solid paddle applicator, applicators for repeated and intermittent use of the cyanoacrylate composition and the like.

In applicators, the cyanoacrylate composition is stored at ambient conditions and can be provided in sterile form.

Compositions

The cyanoacrylate compositions comprising the polymerizable cyanoacrylate esters, the thickening agent(s) and the insoluble antibiotic(s) can be prepared by conventional methods of mixing the appropriate components until homogenous.

The concentration of polymerizable cyanoacrylate ester employed in the composition is preferably from about 50 to about 99 percent by weight based on the total weight of the composition.

The concentration of thickening agent employed is preferably an amount sufficient to form a stable suspension or gel with the polymerizable cyanoacrylate ester and the antibiotic or mixture of antibiotics. This, in turn, correlates with the viscosity of the composition. For example, stable suspensions of insoluble antibiotics are preferably achieved by addition of sufficient thickening agent to provide for a viscosity of from about 50 to 50,000 centipoise at 20° C. For gel forms, it is preferred to add sufficient thickening agent into the composition to impart a viscosity of from about 1,500 to about 1,000,000 centipoise at 20° C. at zero shear. Preferably, the composition is thixotropic such that application of the composition to the tissue is significantly enhanced.

In a particularly preferred embodiment, the composition will comprise from about 0.5 to about 10 percent by weight of the thickening agent based on the total weight of the composition wherein the composition will have a viscosity of from about 50 to about 1,000,000 centipoise at 20° C.

Still further, the concentration of the antibiotic or mixture of antibiotics employed in the composition is sufficient to render the resulting polymeric film antibacterial. That is to say that the concentration of the antibiotic or mixture of antibiotic in the film is sufficient to ensure that the film exhibits antibacterial activity when measured by conventional assays such as that described in Greff, et al.[9] In a preferred embodiment, the composition will comprise from about 0.01 to about 2 percent by weight of the antibiotic or mixtures of antibiotics based on the total weight of the composition.

The cyanoacrylate compositions preferably include a biocompatible plasticizer and such plasticizers are preferably included in the composition from about 10 to 30 weight percent and more preferably from about 18 to 25 weight percent based on the total weight of the composition absent any antimicrobial agent.

Additionally, the cyanoacrylate compositions described herein preferably include a polymerization inhibitor in an effective amount to inhibit premature polymerization of the composition during storage. In a particularly preferred embodiment, this inhibitor is sulfur dioxide which is employed at from about 50 to 500 ppm, preferably 200 to 500 ppm, based on the total weight of the composition absent any antimicrobial agent. Other preferred polymerization inhibitors include glacial acetic acid, free radical inhibitors (e.g., hydroquinones) and the like which can be used alone or in combination with $SO_2$.

The polymerizable cyanoacrylate ester compositions may additionally contain one or more optional additives such as medicaments, colorants, perfumes, anti-diffusion agents, rubber modifiers, modifying agents, etc. In practice, each of these optional additives should be both miscible and compatible with the cyanoacrylate composition and the resulting polymer. Compatible additives are those that do not prevent the use of the cyanoacrylates in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. Medicaments are added as necessary to achieve a desired prophylactic or therapeutic effect. The amount of each of these optional additives employed in the composition is an amount necessary to achieve the desired effect.

Other medicaments suitable for use in conjunction with the cyanoacrylate composition include corticoid steroids such as described by Greff, et al. in U.S. Pat. No. 5,962,010 which is incorporated herein by reference in its entirety and analgesic compounds such as lidocaine. The former reduces inflammation at the tissue site whereas the latter reduces pain. Combinations of a steroid with an analgesic are also covered.

Utility

The methods described herein are useful in forming an antibacterial polymeric film over mammalian tissue. This polymeric film finds particular utility in treating an existing bacterial infection at the tissue site or in inhibiting this tissue from becoming infected with bacteria. Suitable mammals for use in these methods preferably include humans as well as domestic animals such as horses, cows, dogs, sheep, cats, etc.

The following examples illustrate certain embodiments of the invention but is not meant to limit the scope of the claims in any way.

Example 1 below illustrates how the methods of this invention could be practiced.

EXAMPLE 1

A man subject to recurrent skin infections presents himself to the attending clinician with a large area of the inner right thigh that is beginning to redden and itch. The involved area and the surrounding two inches of skin are coated with a gel composition comprising 70% n-butyl cyanoacrylate, 23% di-ethylhexyl phthalate plasticizer, 6% hydrophobic fumed silica, 0.3% neomycin sulfate, 0.15% polymixin B sulfate, and 0.55% bacitracin zinc (all percentages are weight percentages based on the total weight of the composition). The gel spreads easily and sets within 60 seconds to form a coherent flexible polymeric film.

From the foregoing description, various modifications and changes in the composition and method will occur to those skilled in the art. All such modifications coming within the scope of the appended claims are intended to be included therein.

What is claimed is:

1. A polymerizable film-forming cyanoacrylate composition comprising:

from about 50 to 99 weight percent of a polymerizable cyanoacrylate ester based on the total weight of the composition;

an antibacterially effective amount of an antibiotic or a mixture of antibiotics which are insoluble in the polymerizable cyanoacrylate ester; and a sufficient amount of a thickening agent which forms a stable suspension or gel in combination with the cyanoacrylate ester and the antibiotic or the mixture of antibiotics, wherein at least 50% of the suspended material remains in suspension for a period of at least 3 months at 20° C.

2. The polymerizable film-forming cyanoacrylate composition according to claim 1, wherein said composition is characterized as possessing thixotropic properties.

3. The polymerizable film-forming cyanoacrylate composition according to claim 2, wherein at least 50% of the suspended material remains in suspension for a period of at least 6 months.

4. The polymerizable film-forming cyanoacrylate composition according to claim 3, wherein at least 90% of the suspended material remains in suspension for a period of at least 6 months.

5. The polymerizable film-forming cyanoacrylate composition according to claim 1, wherein a mixture of antibiotics is employed in said composition to provide a spectrum of antibacterial activity.

6. The polymerizable film-forming cyanoacrylate composition according to claim 1, wherein said mixture of antibiotics comprises neomycin, polymixin B sulfate, and bacitracin.

7. The composition according to claim 1, wherein said polymerizable cyanoacrylate ester composition comprises a cyanoacrylate ester, which in monomeric form, is represented by formula I:

$$CH_2=C(CN)-COOR$$

where R is selected from the group consisting of:
- alkyl of 1 to 10 carbon atoms,
- alkenyl of 2 to 10 carbon atoms,
- cycloalkyl groups of from 5 to 8 carbon atoms,
- phenyl, 2-ethoxyethyl, 3-methoxybutyl, and
- a substituent of the formula:

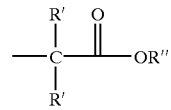

wherein each R' is independently selected from the group consisting of:
- hydrogen and methyl, and R" is selected from the group consisting of:
- alkyl of from 1 to 6 carbon atoms,
- alkenyl of from 2 to 6 carbon atoms,
- alkynyl of from 2 to 6 carbon atoms,
- cycloalkyl of from 3 to 8 carbon atoms,
- aralkyl selected from the group consisting of benzyl, methylbenzyl and phenylethyl,
- phenyl, and
- phenyl substituted with 1 to 3 substituents selected from the group consisting of hydroxy, chloro, bromo, nitro, alkyl of 1 to 4 carbon atoms, and alkoxy of from 1 to 4 carbon atoms.

8. The composition according to claim 7, wherein R is alkyl of from 2 to 10 carbon atoms.

9. The composition according to claim 8, wherein R is alkyl of from 2 to 8 carbon atoms.

10. The composition according to claim 9, wherein R is selected from the group consisting of butyl, pentyl or octyl.

11. The composition according to claim 10, wherein R is n-butyl.

12. The composition according to claim 1 wherein said cyanoacrylate composition further comprises a biocompatible plasticizer.

13. The composition according to claim 12, wherein said biocompatible plasticizer is dioctyl phthalate or acetyl tri-n-butyl citrate.

14. The composition according to claim 13, wherein said cyanoacrylate adhesive composition further comprises a polymerization inhibitor.

15. The composition according to claim 14, wherein said polymerization inhibitor is $SO_2$.

* * * * *